(12) United States Patent
Xiong et al.

(10) Patent No.: US 8,721,549 B2
(45) Date of Patent: *May 13, 2014

(54) FRAME AVERAGING CIRCUIT FOR USE IN AN ULTRASOUND IMAGING SYSTEM

(71) Applicant: Shenzhen Mindray Bio-Medical Electronics Co., Ltd., Shenzhen (CN)

(72) Inventors: Wei Xiong, Shenzhen (CN); Yong Li, Shenzhen (CN); Jianyong Wang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,186

(22) Filed: Oct. 8, 2012

(65) Prior Publication Data

US 2013/0046180 A1    Feb. 21, 2013

Related U.S. Application Data

(63) Continuation of application No. 12/255,570, filed on Oct. 21, 2008, now Pat. No. 8,282,560.

(30) Foreign Application Priority Data

Oct. 22, 2007  (CN) .......................... 2007 1 0166607

(51) Int. Cl.
    *A61B 8/14*  (2006.01)
(52) U.S. Cl.
    USPC ........... 600/454; 600/437; 702/190; 702/199; 348/571; 381/71.1
(58) Field of Classification Search
    USPC ......... 600/309, 407, 419, 437, 438, 443, 455, 600/509, 512; 382/128, 130
    See application file for complete search history.

(56) References Cited

U.S. PATENT DOCUMENTS 5,467,770 A  11/1995  Smith et al.
5,595,179 A   1/1997  Wright et al.

(Continued)

FOREIGN PATENT DOCUMENTS

CN  1207889 A  2/1999
CN  1208599 A  2/1999

OTHER PUBLICATIONS

Office Action dated May 11, 2011 as received in U.S. Appl. No. 12/255,570.

(Continued)

*Primary Examiner* — Unsu Jung
*Assistant Examiner* — Michael N Fisher
(74) *Attorney, Agent, or Firm* — Kory D. Christensen; Stoel Rives LLP (57) ABSTRACT

A frame averaging circuit adapted for a color blood flow frame in a medical ultrasound imaging system. The frame averaging circuit comprises two sections, i.e., a recursive calculation section and a non-recursive section. The recursive calculation section employs an IIR filter in combination with a look-up table, and is adapted for dealing with the cases where no change occurs to the blood flow velocity direction. The non-recursive section compares the blood flow velocity, the energy and the energy prior to wall filtering of the color blood flow echo signal to various threshold values. Different from the recursive calculation section, the non-recursive section is employed when a change occurs to the blood flow velocity direction.

15 Claims, 6 Drawing Sheets

(56) References Cited

U.S. PATENT DOCUMENTS

| | | | |
|---|---|---|---|
| 5,788,635 A * | 8/1998 | Wright et al. | 600/437 |
| 5,823,964 A * | 10/1998 | Liu et al. | 600/454 |
| 5,895,358 A * | 4/1999 | Becker et al. | 600/454 |
| 5,897,502 A * | 4/1999 | Wong et al. | 600/454 |
| 5,899,864 A * | 5/1999 | Arenson et al. | 600/455 |
| 6,123,672 A * | 9/2000 | Miller et al. | 600/455 |
| 6,352,511 B1 * | 3/2002 | Hossack et al. | 600/443 |
| 6,464,640 B1 * | 10/2002 | Guracar et al. | 600/453 |
| 7,139,611 B1 * | 11/2006 | Kroll et al. | 607/28 |
| 2005/0038843 A1 | 2/2005 | LaRocca et al. | |
| 2009/0105593 A1 | 4/2009 | Xiong et al. | |

OTHER PUBLICATIONS

Office Action dated Oct. 11, 2011 as received in U.S. Appl. No. 12/255,570.

Office Action dated Apr. 20, 2012 as received in U.S. Appl. No. 12/255,570.

Notice of Allowance dated Aug. 24, 2012 as received in U.S. Appl. No. 12/255,570.

* cited by examiner

FRAME AVERAGING CIRCUIT FOR USE IN AN ULTRASOUND IMAGING SYSTEM

CROSS-REFERENCE TO RELATED APPLICATIONS

The present application is a continuation of U.S. application Ser. No. 12/255,570, now U.S. Pat. No. 8,282,560, entitled "Frame Averaging Circuit For Use in an Ultrasound Imaging System", filed on Oct. 21, 2008, which claims priority to Chinese Patent Application No. 200710166607.7, entitled "Frame Averaging Circuit for Use in an Ultrasound Imaging System," filed on Oct. 22, 2007, which is incorporated herein by reference.

TECHNICAL FIELD

The present disclosure relates to ultrasound imaging and, more particularly, to a frame averaging circuit for use in an ultrasound imaging system.

BRIEF SUMMARY

A frame averaging circuit adapted for a color blood flow frame in a medical ultrasound imaging system is disclosed.

DETAILED DESCRIPTION

In a medical ultrasound imaging system, for B-mode imaging, the gray scale at a pixel point represents the amplitude of ultrasound echo data in a two-dimensional sectional view, while for color flow imaging, colors represent the movement velocity of red blood cells in a blood vessel or the movement velocity of a tissue. The velocity of blood flowing in the heart and blood vessels may be detected based on the Doppler effect produced by the movement of red blood cells. The ultrasound imaging system estimates the velocity of blood flow by calculating the frequency offset of an ultrasound echo signal, because the frequency offset of the ultrasound echo signal is directly proportional to the movement velocity of red blood cells in a blood vessel. A positive frequency offset signifies that the red blood cells are moving in the blood vessel towards the probe scan direction, while a negative frequency offset signifies that the red blood cells are moving in the blood vessel away from the probe scan direction. The frequency offset is then color coded to form a two-dimensional color blood flow diagram, wherein different colors represent different magnitudes and directions of a blood flow velocity. The color blood flow image is typically displayed by being superposed on the B-mode image, the B-mode image providing information on the outside of the blood vessel, while the blood flow image provides information on the inside of the blood vessel, thereby forming a two-dimensional color image.

Figure 1:
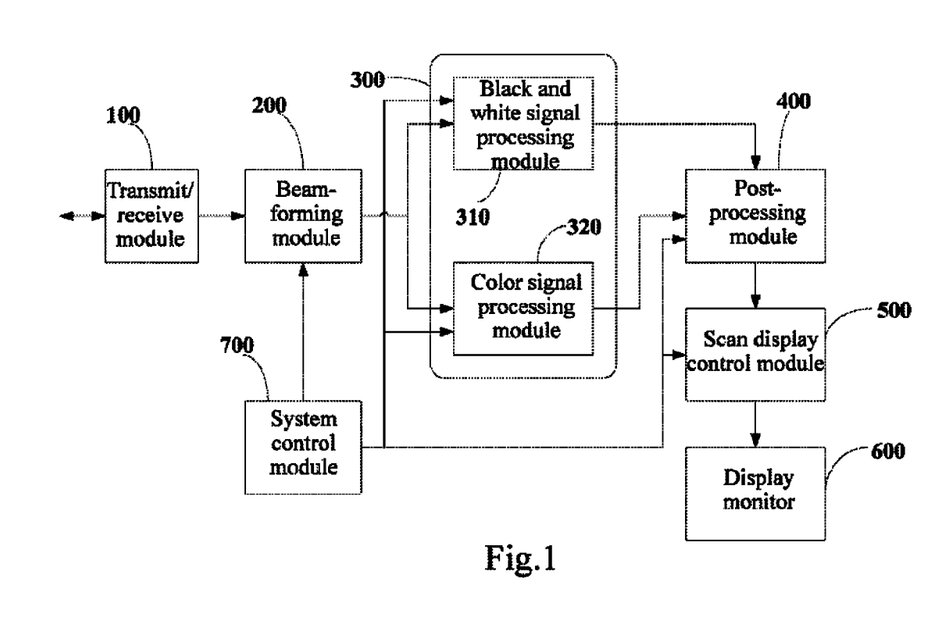
FIG. 1 is a structural block diagram of a medical ultrasound imaging system.

As shown in FIG. 1, a typical medical ultrasound imaging system includes the following components: a transmit/receive module 100, a beamforming module 200, a signal processing module 300, a post-processing module 400, a scan display control module 500, a display monitor 600, and a system control module 700. The system control module 700 may be embodied as a software and hardware interface, including a software controller and a hardware controller. The hardware controller receives and processes parameters written by software, and converts them into control signals for use in the beamforming module 200, the signal processing module 300, the post-processing module 400 and the scan display control module 500. Besides, the system control module 700 generally controls the timing and operation of the whole system through a hardware control and scan control bus.

In one embodiment, ultrasound echo data is first received at the transmit/receive module 100, which may be, for example, a probe, and passes through an A/D converter before entering into the beamforming module 200, where the ultrasound echo data is further processed. In view of the scan mode, two different types of data are generated from the ultrasound echo data in the beamforming module 200. One is intended for B-mode imaging, and the other is for color blood flow imaging. The ultrasound echo data for B-mode imaging is then inputted into a black and white signal processing module 310, while the ultrasound echo data for color blood flow imaging is instead inputted into a color signal processing module 320. The black and white signal processing module 310 and the color signal processing module 320 each process the respective inputted ultrasound echo data based on system parameters and control signals, and then output the respective processed result into the post-processing module 400. The post-processing module 400 outputs a result to the scan display control module 500, which subsequently converts the ultrasound imaging result into standard video data. The video data is finally displayed on the display monitor 600.

To be more specific, the black and white signal processing module 310 may to perform operations, such as logarithmic compression, envelope signal detection and downsampling, on the ultrasound echo data for B-mode imaging, which is outputted from the beamforming module 200, to turn the data into an 8-bit gray scale data stream. Each data point in the data stream corresponds to each sampling point in the scan line, so the magnitude of the data represents the gray scale of the corresponding point.

The color signal processing module 320 is to calculate velocity, variance, energy, and energy prior to wall filtering at any sampling point in a blood flow in the scan section based on the Doppler effect produced by the movement of red blood cells by means of an autocorrelation algorithm. The data components may also be expressed in an 8-bit format in one embodiment.

The post-processing module 400 performs operations, such as Cine storage, frame averaging and priority coding, on the data outputted from the black and white signal processing module 310 and the data from the color signal processing module 320. The frame averaging according to the present disclosure is done in the post-processing module 400. The processed result from the post-processing module 400 is outputted to the scan display control module 500.

Conventional ultrasound imaging systems typically use a frame averaging process, because it can reduce the unfavorable effect of random noise. Generally, the frame averaging process is implemented by an infinite impulse response (IIR)

filter. The IIR filter employs the currently input image data (i.e., the image data of a current frame) and the image data of a previous frame. The frame averaging calculation is as follows:

$$Y(n)=A*Y(n-1)+(1-A)*X(n)$$

where, Y(n) is the result of the frame averaging of the current frame; A is a constant; Y(n−1) is the result of the frame averaging of the previous frame; and X(n) is the current frame of image.

Although noise and speckles are effectively reduced by such frame averaging calculation during the color blood flow imaging, legitimate velocity signals are undesirably averaged over time. Thus, slight changes in velocity and low velocity blood flows cannot be detected. Such frame averaging calculations are especially insensitive to a rapid change in blood flow velocity direction, which, however, plays a critical role in practical clinical diagnosis. In addition, constant A reduces the velocity attenuation, so that changes in movement cannot be reflected rapidly. Hence, it is possible that when the probe has left a moving object, the blood flow is still displayed in the blood flow image.

U.S. Pat. No. 5,595,179, discloses an easily-implemented frame averaging structure including two sections. One is a recursive calculation section, and the other is a non-recursive calculation section. An IIR filter is used in the recursive calculation section, which has a constant coefficient, while a FIR filter is used in the non-recursive calculation section, the coefficient of which may be obtained from a look-up table. This structure has a greatly improved performance compared to existing structures, but still suffers from obvious disadvantages. It is incapable of dealing with rapid direction changes in blood flows, especially of blood flows at a low velocity. Besides, when a blood flow velocity is aliased, the calculated velocity value derives from the real velocity.

U.S. Pat. No. 5,897,502 discloses a frame averaging structure in which an IIR filter uses a simple and constant coefficient that is not. The disclosed technique determines whether to output a current velocity value or a previous processed velocity value by comparing the current velocity value to a threshold. Unfortunately, the disclosed technique does not accommodate velocity aliasing. The proposed structure is sensitive to fast changes in velocity direction, but not in the case where no change occurs to the velocity direction, for example, it is unable to effectively eliminate noise in echo data. Besides, the proposed structure fails to reflect a rapid decrease of velocity.

So far, the existing frame averaging structures generally include a recursive calculation section and a non-recursive calculation section. Most conventional techniques try to improve the look-up table in the recursive calculation section and the algorithm in the non-recursive calculation section by attempting to reduce noise and flash artifacts in a blood flow image, thereby improving the reaction speed to any change in velocity direction, and reducing the effect caused by aliasing on a color blood flow image.

In summary, the prior graphical processing techniques for the ultrasound blood flow imaging are subjected to the following shortcomings:

1. Flash artifacts exist in the blood flow image to be displayed, which adversely affects the image quality;

2. Aliasing makes unfavorable effect on the blood flow image; and

3. It is impossible to reflect actual changes in blood blow velocity direction and actual blood flow conditions in real time.

The present disclosure overcomes the aforementioned problems by providing an improved frame averaging circuit for use in an ultrasound imaging system. In one embodiment, the frame average circuit includes a recursive calculation section for filtering a blood flow velocity of a current frame and a frame-averaged blood flow velocity of a previous frame. The frame averaging circuit may also include a non-recursive section for making determinations as to the blood flow velocity of the current frame and determining whether to output the blood flow velocity of the current frame or to output an output of the recursive calculation section as a frame-averaged blood flow velocity of the current frame.

In one embodiment, the recursive calculation section includes a filter and a coefficient providing unit for providing a coefficient to the filter. The coefficient providing unit may include a memory for storing a look-up table which stores the coefficient of the filter and an address generator for generating an address for the look-up table based on the blood flow velocity of the current frame in combination with the frame-averaged blood flow velocity of the previous frame, based on which the coefficient of the filter is looked up in the memory. In one configuration, the filter is an IIR filter.

In one embodiment, the non-recursive section includes a first threshold comparator for comparing each of the blood flow components of the current frame with a corresponding threshold value, and, if each of the blood flow components of the current frame is larger than the corresponding threshold value, determining that the blood flow velocity of the current frame is legitimate, otherwise, determining that the blood flow velocity of the current frame corresponds to noise.

The non-recursive section may also include a second threshold comparator for comparing the blood flow velocity of the current frame with the frame-averaged blood flow velocity of the previous frame to determine whether the following conditions occur: the frame-averaged blood flow velocity of the previous frame is aliased, or the blood flow velocity of the current frame is flicker noise.

In one embodiment, the non-recursive section includes a first combiner for combining the output of the first threshold comparator with the output of the second threshold comparator. The non-recursive section may also include a first selector for selecting whether to output the blood flow velocity of the current frame or to output the output of the recursive calculation section based on the output of the first combiner, wherein if the blood flow velocity of the current frame is legitimate and one of the conditions occurs, or if the blood flow velocity of the current frame corresponds to noise, the first selector selects to output the output of the recursive calculation section, otherwise, selects to output the blood flow velocity of the current frame.

The non-recursive section may further include a velocity comparator for comparing the absolute value of the blood flow velocity of the current frame with the absolute value of the output of the recursive calculation section, wherein if the absolute value of the blood flow velocity of the current frame is larger than the absolute value of the output of the recursive calculation section, it is determined that the blood flow velocity of the current frame is larger than the frame-averaged blood flow velocity of the previous frame, otherwise, it is determined that the blood flow velocity of the current frame is smaller than the frame-averaged blood flow velocity of the previous frame.

In one embodiment, the non-recursive section includes a second selector for selecting whether to output the blood flow velocity of the current frame or to output the output of the recursive calculation section based on the output of the velocity comparator, wherein if the blood flow velocity of the current frame is larger than the frame-averaged blood flow velocity of the previous frame, the output of the recursive calculation section is selected to be outputted, otherwise, the blood flow velocity of the current frame is selected to be outputted.

The non-recursive section may include a velocity direction determining unit for determining whether the blood flow velocity of the current frame is in the same direction as the frame-averaged blood flow velocity of the previous frame. In addition, the non-recursive section may include a third selector for selecting whether to output the output of the first selector or to output the output of the second selector based on the output of the velocity direction determining unit, wherein if the blood flow velocity of the current frame is determined to be in the same direction as the frame-averaged blood flow velocity of the previous frame, the output of the second selector is selected to be outputted, otherwise, the output of the first selector is selected to be outputted. In one configuration, the first combiner is an AND gate.

According to one embodiment, the first threshold comparator includes a velocity threshold comparator for comparing the blood flow velocity of the current frame with a velocity threshold value; a first energy threshold comparator for comparing the energy of the current frame with a first energy threshold value; a second energy threshold comparator for comparing the energy of the current frame prior to wall filtering with a second energy threshold value; and a second combiner for combining the output of the velocity threshold comparator, the output of the first energy threshold comparator and the output of the second energy threshold comparator. The second combiner may be embodied as an AND gate.

In one embodiment, the second threshold comparator includes a velocity difference threshold comparator for comparing the absolute value of a difference between the blood flow velocity of the current frame and the frame-averaged blood flow velocity of the previous frame with a velocity difference threshold value, wherein if the absolute value of said difference is larger than the velocity difference threshold value, it is determined that the frame-averaged blood flow velocity of the previous frame is aliased.

The second threshold comparator may also include a velocity absolute value comparator for comparing the absolute value of the blood flow velocity of the current frame and the absolute value of the frame-averaged blood flow velocity of the previous frame, wherein if the absolute value of the blood flow velocity of the current frame is smaller than the absolute value of the frame-averaged blood flow velocity of the previous frame, it is determined that the blood flow velocity of the current frame is flicker noise.

In addition, the second threshold comparator may include a third combiner for combining the output of the velocity difference threshold comparator and the output of the velocity absolute value comparator. In one embodiment, the third combiner is an XOR gate.

The present disclosure has the following advantages compared to the prior techniques:
 1. effectively eliminating flash artifacts in the blood flow image;
 2. effectively reducing the adverse effect on echo data caused by noise;
 3. reducing the adverse effect on the image caused by echo data aliasing;
 4. reflecting actual blood flow conditions in real time; and
 5. timely reflecting any changes in blood flow velocity direction.

The frame averaging circuit according to the present disclosure may include two sections. One is a recursive calculation section, which employs an IIR filter to filter both the blood flow velocity of a current frame and the frame-averaged blood flow velocity of a previous frame. The filter coefficient as employed is obtained from a look-up table. The look-up table receives as inputs the blood flow velocity of the current frame and the frame-averaged blood flow velocity of the previous frame. The recursive calculation section is excellent in dealing with changes when the blood flows in the same direction. The other is a non-recursive section, which makes determinations as to the blood flow velocity of the current frame. For example, the non-recursive section compares the energy, the energy prior to wall filtering, and the blood flow velocity of the current frame with a corresponding threshold value. The non-recursive section is excellent in controlling the blood flow velocity output when the direction in which the blood flows is changed.

By using the disclosed frame averaging circuit to process the blood flow velocity, the output blood flow velocity may correctly reflect real changes in the blood flow. This is because the disclosed frame averaging circuit properly handles velocity changes both when the blood flows in the same direction and when the direction in which the blood flows is changed. When the blood flows in the same direction, the IIR filter effectively reduces the unfavorable effect on the blood flow signal caused by noise. When the direction in which the blood flows is changed, due to use of a threshold by the non-recursive section, fast changes in blood flow velocity may be reflected in real time, and moreover it is less likely that the image will be adversely affected by the velocity changes caused by other factors.

Figure 2:
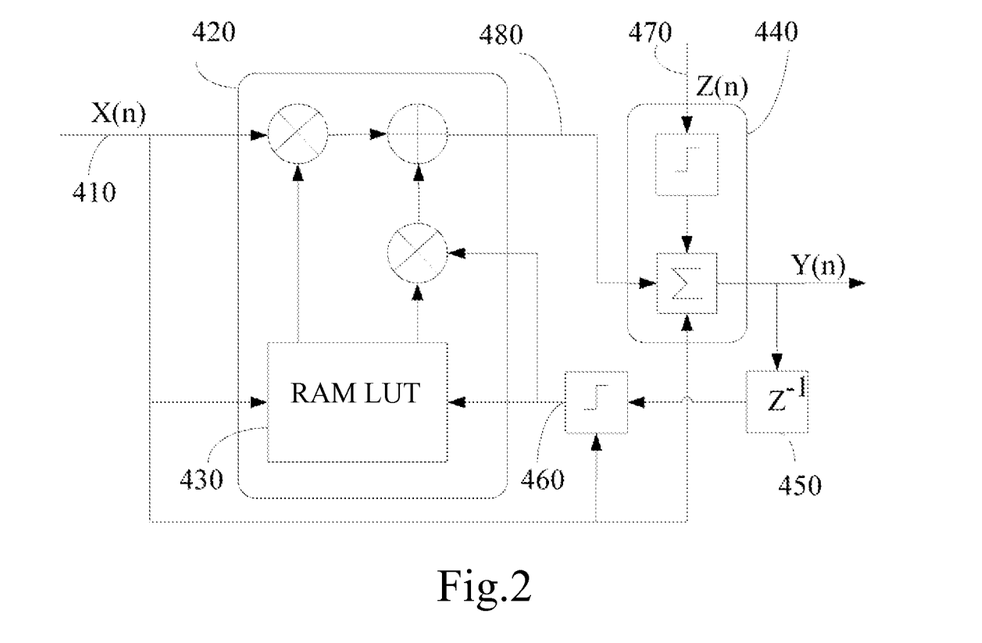
FIG. 2 is a structural block diagram of a frame averaging circuit.

One aspect of the present disclosure is a frame averaging process included in color blood flow signal processing of a medical ultrasound imaging system. As shown in FIG. 2, the frame averaging circuit according to the present disclosure may include two sections, a recursive calculation section 420 and a non-recursive section 440. The blood flow velocity signal X(n) 410 of a current frame is fed into both the filter of the recursive calculation section 420 and the selector of the non-recursive section 440. The filter of the recursive calculation section 420 is given four inputs, two are calculated data, and the other two are coefficients. One of the two calculated data is the blood flow velocity value X(n) 410 of the current frame, and the other is the blood flow velocity value 460 of a previous frame, which has been frame averaged. The frame-averaged blood flow velocity value 460 of the previous frame is stored in a random access memory. When the blood flow velocity value X(n) 410 of the current frame is inputted into the filter of the recursive calculation section 420, the frame-averaged blood flow velocity value 460 of the previous frame is read from the random access memory for the filtering calculation. The two coefficients concerned are obtained from the random access memory look-up table (RAM LUT) 430 of the recursive calculation section 420, both of which are a function of value X(n) 410 and value 460. The non-recursive section 440 receives an output value 480 from the recursive calculation section 420, and compares it to a threshold value. The non-recursive section 440 further includes a threshold comparator operable to receive various calculated blood flow components Z(n) 470 (including the energy, the energy prior to wall filtering, and the velocity) of the current frame, compare the input data to respective threshold values, and output a comparison result. The selector of the non-recursive section 440 is operable to control the output result of the frame averaging circuit based on the comparison result in combination with the change in velocity direction. That is, the selector of the non-recursive section 440 determines whether the frame averaging circuit is to output the blood flow velocity value of the current frame or the velocity value filtered by the filter of the recursive calculation section 420 (i.e., the output value outputted from the recursive calculation section 420). A delay unit 450 allows using the frame-averaged blood flow velocity of the previous frame via a delay of one frame.

Figure 3:
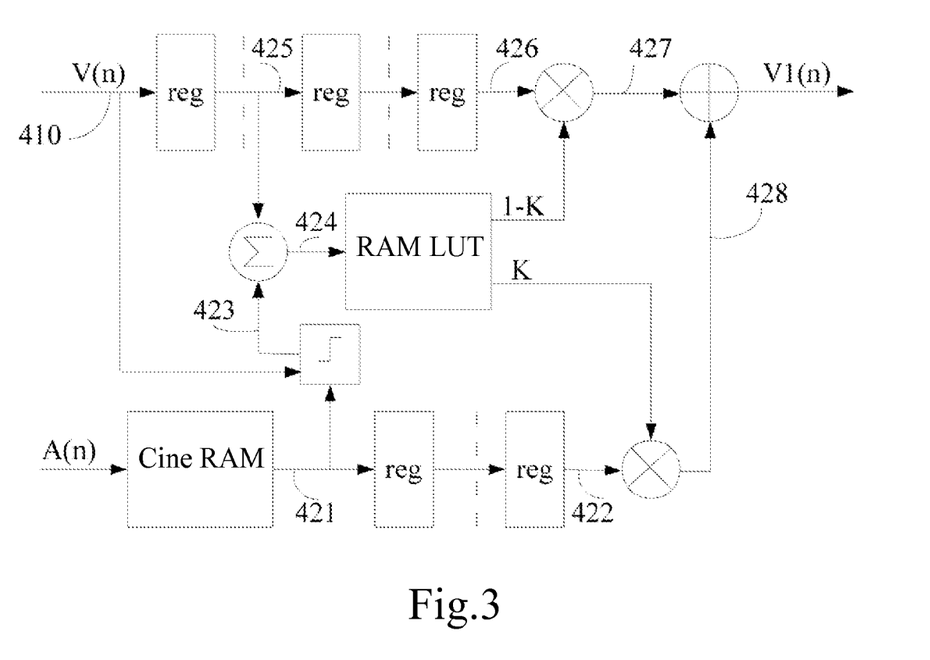
FIG. 3 is a circuit diagram of a recursive calculation.

As shown in FIG. 3, the recursive calculation section may include an IIR filter and a look-up table. In one embodiment, when given a new frame of data (i.e. the current frame), the hardware controller in the system control module generates an address signal A(n) for a cine random access memory (Cine RAM) based on the new frame of data, and reads the frame-averaged blood flow velocity value 421 of the previous frame from the Cine RAM. The blood flow velocity value 421 is then compared to a threshold value, thus generating a processed blood flow velocity value 423. The blood flow velocity value 423 is combined with the registered blood flow velocity value 425 of the current frame, thus generating a look-up table address 424. Corresponding filter coefficients 1-K and K are read from the RAM LUT based on the look-up table address 424. The filter coefficients 1-K and K are respectively multiplied by the registered blood flow velocity value 426 of the current frame and the registered frame-averaged blood flow velocity value 422 of the previous frame to lead to give values 427 and 428, which are then summed to give the output V1(n) of the recursive calculation section. V1(n) is registered before being inputted into the non-recursive section for further processing. As a result of the filtration, data representing color blood flow conditions is less likely affected by noise and other corrupt signals, thus having its legitimate components maintained.

Figure 4:
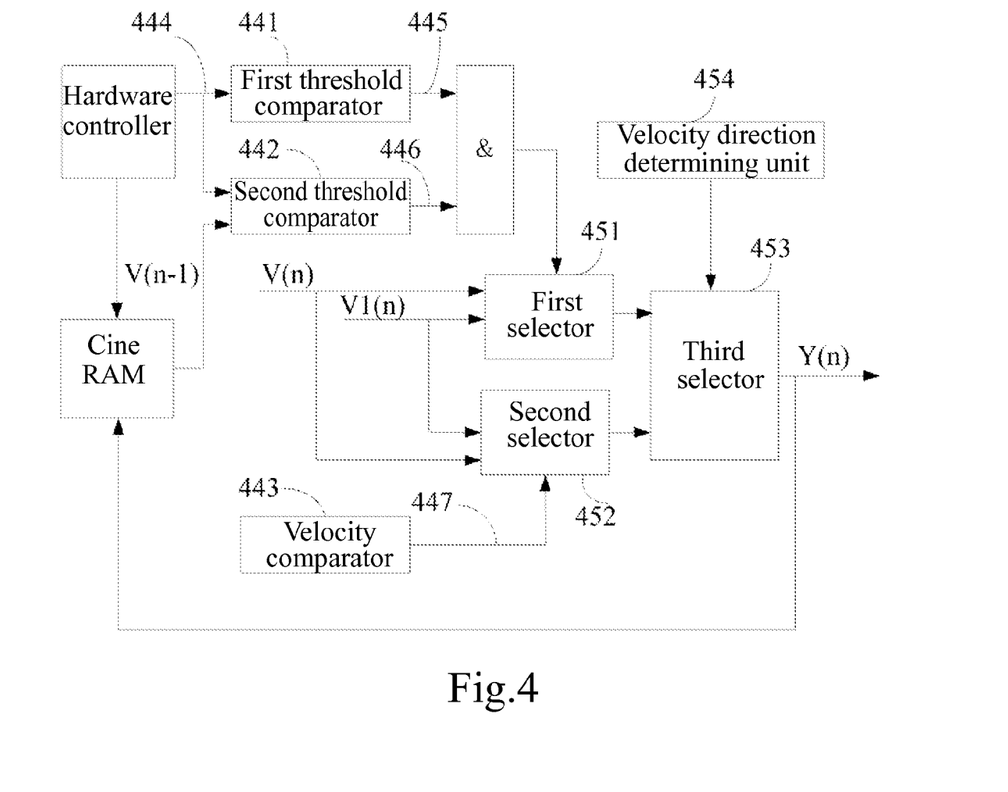
FIG. 4 is a structural block diagram of a non-recursive calculation.

The non-recursive section is shown in greater detail in FIG. 4. In one embodiment, the hardware controller writes various threshold values into a first threshold comparator 441 and a second threshold comparator 442 via a node 444. The first threshold comparator 441 may be responsible for comparing the currently input blood flow components, such as the energy, the velocity and the energy prior to wall filtering, to corresponding threshold values, and feeding an output result 445 into an AND logic. The second threshold comparator 442 may be responsible for comparing blood flow velocities of two consecutive frames of echo data with one another, and also feeding a comparison result 446 into the AND logic. The AND logic outputs a control signal to control a first selector 451. A velocity comparator 443 compares the current echo velocity V(n) to the output V1(n) of the filter, and outputs a comparison result 447 to control a second selector 452. A velocity direction determination unit 454 compares the direction of the current echo velocity with that of the frame-averaged blood flow velocity of the previous frame, and outputs a comparison result to control a third selector 453. Finally, the third selector outputs the frame-averaged result Y(n). The first threshold comparator, the second threshold comparator and the velocity comparator will be described in details below.

Figure 5:
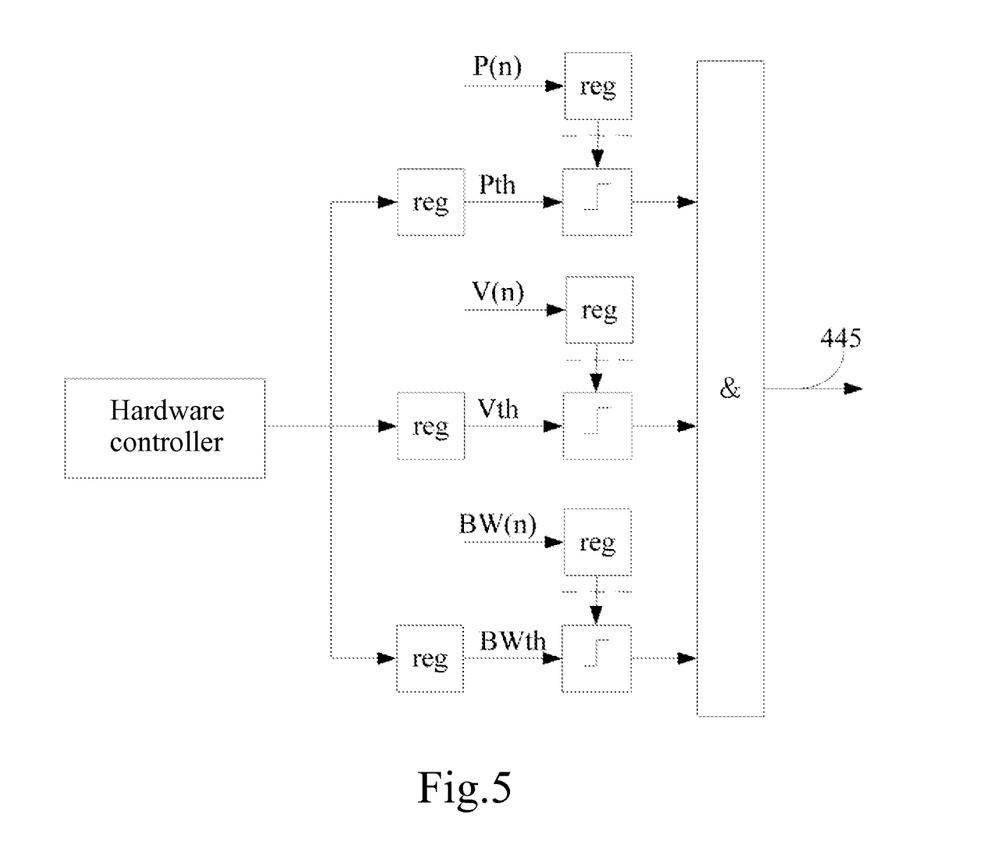
FIG. 5 is a circuit diagram of a first threshold comparator.

The circuit of the first threshold comparator is shown in FIG. 5. In one embodiment, when the velocity direction is changed, the first threshold comparator compares to a corresponding threshold value the velocity, the energy, and the energy prior to wall filtering of the current frame of echo data, to determine whether all of the components of the current frame of echo data simultaneously meet a requirement. If the requirement is met, i.e., if the velocity V(n), the energy P(n), and the energy prior to wall filtering BW(n) of the current frame of echo data are larger than a velocity threshold value Vth, a first energy threshold value Pth and a second energy threshold value BWth, respectively, it is determined that the occurred change in velocity is a valid change, otherwise, it is considered as the effect of noise, which should be eliminated.

Figure 6:
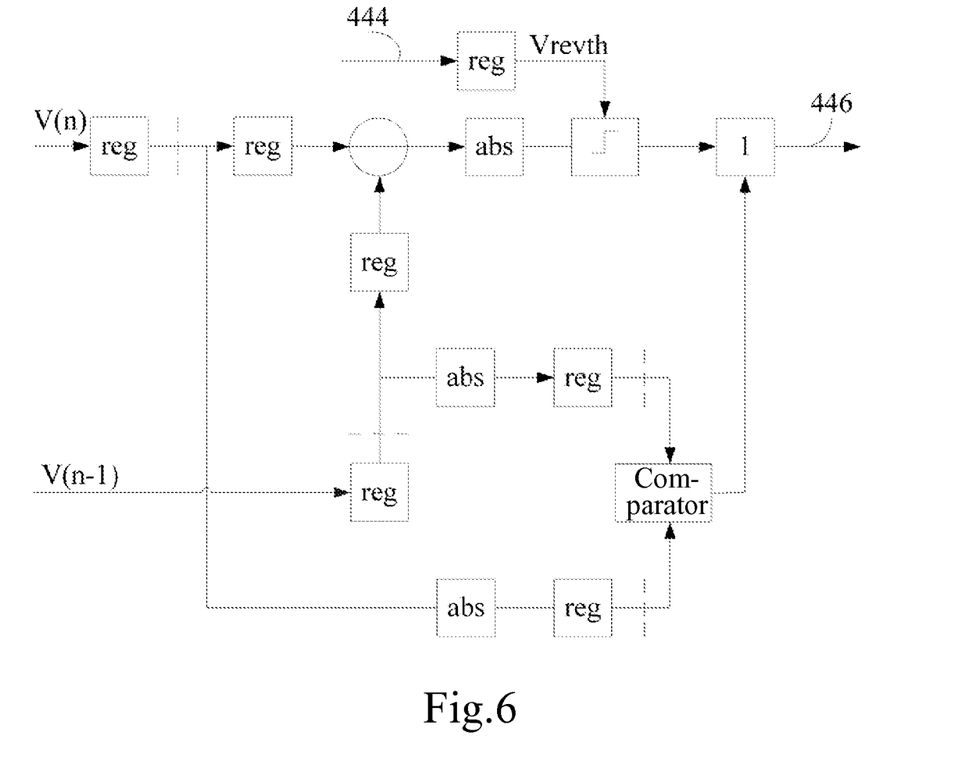
FIG. 6 is a circuit diagram of a second threshold comparator.

The circuit of the second threshold comparator is shown in FIG. 6. In one embodiment, when the velocity direction is changed, the second threshold comparator compares the blood flow velocity value V(n) of the current frame with the frame-averaged blood flow velocity value V(n-1) of the previous frame. The second threshold comparator comprises a velocity difference threshold comparator, a velocity absolute value comparator and an AND-OR gate. The velocity difference threshold comparator compares the absolute value (|V(n)-V(n-1)|) of the difference between the blood flow velocity V(n) of the current frame and the frame-averaged blood flow velocity V(n-1) of the previous frame with a velocity difference threshold value Vrevth. If the absolute value |V(n)-V(n-1)| is larger than the velocity difference threshold value Vrevth, it is determined that aliasing occurs to the frame-averaged blood flow velocity of the previous frame. The velocity absolute value comparator compares the absolute value |V(n)| of the blood flow velocity V(n) of the current frame to the absolute value |V(n-1)| of the frame-averaged blood flow velocity V(n-1) of the previous frame. If |V(n)| is smaller than |V(n-1)|, it is determined that the blood flow velocity of the current frame is flicker noise.

In one embodiment, the AND-OR gate combines the output from the velocity difference threshold comparator with the output from the velocity absolute value comparator. Due to the comparison conducted by the velocity difference threshold comparator, it is possible to determine whether aliasing occurs to the frame-averaged blood flow velocity of the previous frame, or the velocity direction is changed. Due to the comparison conducted by the velocity absolute value comparator, a determination may be made as to whether the velocity is aliased or flicker noise occurs, because the blood flow velocity value of the flicker noise is smaller than the normal blood flow velocity value. By comparing the blood flow velocity of the current frame with the frame-averaged blood flow velocity of the previous frame, it is possible to reduce the unfavorable effect of noise on the image.

Figure 7:
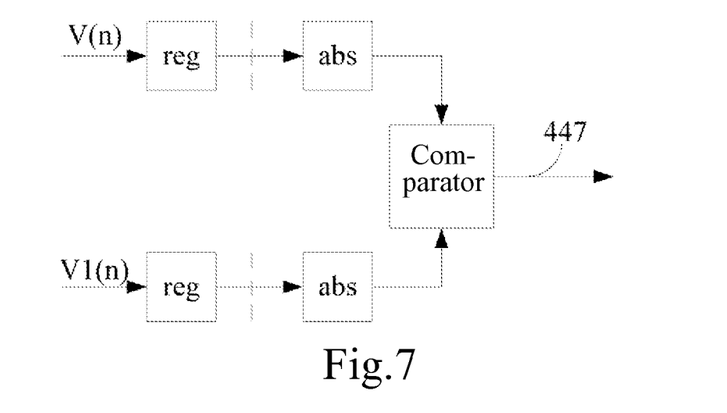
FIG. 7 is a circuit diagram of a velocity comparator.

The circuit of the velocity comparator is shown in FIG. 7. In one embodiment, the velocity comparator compares the absolute value |V(n)| of the blood flow velocity V(n) of the current frame with the absolute value |V1(n)| of the output V1(n) of the recursive calculation section. If |V(n)| is larger than |V1(n)|, it is determined that V(n) is larger than the frame-averaged blood flow velocity V(n-1) of the previous frame, otherwise, V(n) is smaller than the frame-averaged blood flow velocity V(n-1) of the previous frame. The circuit is particularly applicable in the circumstance where the velocity direction remains unchanged, therefore capable of detecting blood flow at a low velocity. If V(n) is larger than V1(n), it is indicated that an accelerating blood flow is detected, otherwise, it is indicated that a decelerating blood flow is detected.

Now returning to FIG. 4, if the blood flow velocity of the current frame is legitimate and one of the following conditions occurs: the frame-averaged blood flow velocity of the previous frame is aliased, or the blood flow velocity of the current frame is flicker noise; or if the blood flow velocity of the current frame corresponds to noise, the first selector 451 outputs the result calculated by the recursive calculation section; otherwise, the output of the first selector 451 is set to the blood flow velocity of the current frame. If the blood flow velocity of the current frame is larger than the frame-averaged blood flow velocity of the previous frame, the second selector 452 outputs the result calculated by the recursive calculation section; otherwise, the output of the second selector 452 is set to the blood flow velocity of the current frame. If the blood flow velocity of the current frame is in the same direction as the frame-averaged blood flow velocity of the previous frame, the third selector 453 outputs the output of the second selector; otherwise, the third selector 453 outputs the output of the first selector.

Therefore, the frame averaging circuit according to the present disclosure is capable of reducing unfavorable effect incurred by noise, while reflecting changes in blood flow velocity in real time. In addition, the frame averaging circuit according to the present disclosure is capable of separately processing the blood flow velocity dependent on whether or not the blood flow velocity direction is changed. When no change occurs to the velocity direction, a dedicated processing circuit will be enabled to reduce the effect of noise; when a change occurs to the velocity direction, a different dedicated processing circuit will be activated to determine whether or not the change in velocity direction is effective, thus better reflecting changes in blood flow velocity in real time.

In summary, the present disclosure provides a frame averaging circuit adapted for a color blood flow frame in a medical ultrasound imaging system. The frame averaging circuit comprises two sections, i.e., a recursive calculation section and a non-recursive section. The recursive calculation section employs an IIR filter in combination with a look-up table, and is adapted for dealing with the cases where no change occurs to the blood flow velocity direction. The non-recursive section compares the blood flow velocity, the energy, and the energy prior to wall filtering of the color blood flow echo signal to various threshold values. Different from the recursive calculation section, the non-recursive section is employed when a change occurs to the blood flow velocity direction. The disclosed circuit effectively reduces flash artifacts in echo data and unfavorable effect of noise on a color blood flow image; rapidly reflects changes in blood flow velocity in real time; and determines any aliasing to the blood flow velocity, thereby rendering a real blood flow image that reflects actual blood flow conditions.

The present disclosure has been applied to a commercial color ultrasonic apparatus. By post-processing the color blood flow echo data, the following advantages may be achieved: the displayed color blood flow image can more vividly reflect changes in blood flow in a blood vessel; effective color blood flow echo velocity signals can be preserved; any flash artifacts in the blood flow image can be eliminated; free noise in the blood flow image can be reduced; and even when the blood flow velocity is aliased, the modality of the blood flow velocity can be correctly reflected, thereby improving the quality of the color blood flow image.

Although the invention has been described above with reference to the specific embodiments thereof, it is not intended that the invention be limited to the above-mentioned embodiments. Various modifications and alternations may be made to the present invention without departing from the scope of the present invention. The scope of the present disclosure is defined by the appended claims. Such words as "first", "second," and "third" used in the description and the claims are merely illustrative and should by no means be considered as restrictive.

What is claimed is:

1. A frame averaging circuit for use in an ultrasound imaging system, comprising:
   a recursive calculation circuit configured to filter a blood flow velocity of a current frame to output a current frame-averaged blood flow velocity based on the current frame and a frame averaged blood flow velocity of a previous frame; and
   a non-recursive circuit configured to determine whether to output the blood flow velocity of the current frame or to output the current frame-averaged blood flow velocity calculated by the recursive calculation circuit.

2. The circuit according to claim 1, wherein the recursive calculation circuit comprises:
   a filter; and
   a coefficient providing circuit configured to provide a coefficient to the filter.

3. The circuit according to claim 2, wherein the coefficient providing circuit comprises:
   a memory configured to store a look-up table which stores the coefficient of the filter; and
   an address generator circuit configured to generate an address for the look-up table based on the blood flow velocity of the current frame in combination with the frame-averaged blood flow velocity of the previous frame, based on which the coefficient of the filter is looked up in the memory.

4. The circuit according to claim 2, wherein the filter is an infinite impulse response (IIR) filter.

5. The circuit according to claim 1, wherein the non-recursive circuit comprises:
   a first threshold comparator circuit configured to compare each of blood flow components of the current frame with a corresponding threshold value, and, if each of the blood flow components of the current frame is larger than the corresponding threshold value, determining that the blood flow velocity of the current frame does not correspond to noise, otherwise, determining that the blood flow velocity of the current frame corresponds to noise.

6. The circuit according to claim 5, wherein the non-recursive circuit further comprises:
   a second threshold comparator circuit configured to compare the blood flow velocity of the current frame with the frame-averaged blood flow velocity of the previous frame to determine whether the following conditions occur:
      the frame-averaged blood flow velocity of the previous frame is aliased, or
      the blood flow velocity of the current frame is flicker noise; and
   a first combiner circuit configured to combine the output of the first threshold comparator circuit with the output of the second threshold comparator circuit.

7. The circuit according to claim 6, wherein the non-recursive circuit further comprises:
   a first selector circuit configured to select whether to output the blood flow velocity of the current frame or to output the output of the recursive calculation circuit based on the output of the first combiner circuit, wherein if the blood flow velocity of the current frame is legitimate and one of the conditions occurs, or if the blood flow velocity of the current frame corresponds to noise, the first selector circuit selects to output the output of the recursive calculation circuit, otherwise, selects to output the blood flow velocity of the current frame.

8. The circuit according to claim 7, wherein the non-recursive circuit further comprises:
   a velocity comparator circuit configured to compare the absolute value of the blood flow velocity of the current frame with the absolute value of the output of the recursive calculation circuit, wherein if the absolute value of the blood flow velocity of the current frame is larger than the absolute value of the output of the recursive calculation circuit, it is determined that the blood flow velocity of the current frame is larger than the frame-averaged blood flow velocity of the previous frame, otherwise, it is determined that the blood flow velocity of the current frame is smaller than the frame-averaged blood flow velocity of the previous frame.

9. The circuit according to claim 8, wherein the non-recursive circuit further comprises:
a second selector circuit configured to select whether to output the blood flow velocity of the current frame or to output the output of the recursive calculation circuit based on the output of the velocity comparator circuit, wherein if the blood flow velocity of the current frame is larger than the frame-averaged blood flow velocity of the previous frame, the output of the recursive calculation circuit is selected to be outputted, otherwise, the blood flow velocity of the current frame is selected to be outputted.

10. The circuit according to claim 9, wherein the non-recursive circuit further comprises:
a velocity direction determining circuit configured to determine whether the blood flow velocity of the current frame is in the same direction as the frame-averaged blood flow velocity of the previous frame; and
a third selector circuit configured to select whether to output the output of the first selector circuit or to output the output of the second selector circuit based on the output of the velocity direction determining circuit, wherein if the blood flow velocity of the current frame is determined to be in the same direction as the frame-averaged blood flow velocity of the previous frame, the output of the second selector circuit is selected to be outputted, otherwise, the output of the first selector circuit is selected to be outputted.

11. The circuit according to claim 6, wherein the first combiner circuit is an AND gate.

12. The circuit according to claim 5, wherein the first threshold comparator circuit comprises:
a velocity threshold comparator circuit configured to compare the blood flow velocity of the current frame with a velocity threshold value;
a first energy threshold comparator circuit configured to compare the energy of the current frame with a first energy threshold value;
a second energy threshold comparator circuit configured to compare the energy of the current frame prior to wall filtering with a second energy threshold value; and
a second combiner circuit configured to combine the output of the velocity threshold comparator circuit, the output of the first energy threshold comparator circuit and the output of the second energy threshold comparator circuit.

13. The circuit according to claim 12, wherein the second combiner circuit is an AND gate.

14. The circuit according to claim 6, wherein the second threshold comparator circuit comprises:
a velocity difference threshold comparator circuit configured to compare the absolute value of a difference between the blood flow velocity of the current frame and the frame-averaged blood flow velocity of the previous frame with a velocity difference threshold value, wherein if the absolute value of said difference is larger than the velocity difference threshold value, it is determined that the frame-averaged blood flow velocity of the previous frame is aliased;
a velocity absolute value comparator circuit configured to compare the absolute value of the blood flow velocity of the current frame and the absolute value of the frame-averaged blood flow velocity of the previous frame, wherein if the absolute value of the blood flow velocity of the current frame is smaller than the absolute value of the frame-averaged blood flow velocity of the previous frame, it is determined that the blood flow velocity of the current frame is flicker noise; and
a third combiner circuit configured to combine the output of the velocity difference threshold comparator circuit and the output of the velocity absolute value comparator circuit.

15. The circuit according to claim 14, wherein the third combiner circuit is an XOR gate.

* * * * *